United States Patent [19]

Broger et al.

[11] Patent Number: 5,710,322
[45] Date of Patent: Jan. 20, 1998

[54] OPTICALLY ACTIVE IMINOCARBOXYLIC ACID DERIVATIVES

[75] Inventors: Emil Albin Broger, Magden; Rudolf Schmid, Arlesheim, both of Switzerland

[73] Assignee: Hoffmann-La Roche Inc., Nutley, N.J.

[21] Appl. No.: 808,297

[22] Filed: Feb. 28, 1997

[30] Foreign Application Priority Data

Mar. 29, 1996 [EP] European Pat. Off. .............. 96105034

[51] Int. Cl.[6] .................................................. C07C 249/00
[52] U.S. Cl. ................................................ 562/440; 564/164
[58] Field of Search .............................. 562/440; 564/164

[56] References Cited

FOREIGN PATENT DOCUMENTS

| 497 192 | 8/1992 | European Pat. Off. . |
| 664 284 | 7/1995 | European Pat. Off. . |
| 62-207245 | 9/1987 | Japan . |

OTHER PUBLICATIONS

Bommarius, A.S., et al., *Tetrahedron: Asymmetry*, 6(12):2851–2888 (1995).
Hiskey, R.G., et al., *J.A.C.S.*, 83:4798–4800 (1961).
Schellenberger, A., et al., *Hoppe–Seyler's Z. Phys. Chem.*, 329:149–162 (1962).
Turner, N.J., et al., *Tetrahedron Letters*, 36(7):1113–1116 (1995).
Ikota, *Chem. Pharm. Bull.*, vol. 31, pp. 887–894, 1983.

*Primary Examiner*—Michael L. Shippen
*Attorney, Agent, or Firm*—George W. Johnston; Dennis P. Tramaloni; Alan P. Kass

[57] ABSTRACT

The compounds of the formula

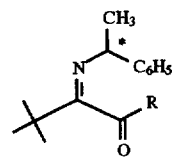

wherein

R is OH, $NH_2$, lower-alkyl-NH or phenyl-lower alkyl-NH are presented. These compounds can be catalytically hydrogenated to the corresponding α-aminocarboxylic acid derivatives which are intermediates in the synthesis of therapeutic pseudopeptides.

18 Claims, No Drawings

OPTICALLY ACTIVE IMINOCARBOXYLIC ACID DERIVATIVES

The invention is concerned with compounds of the formula

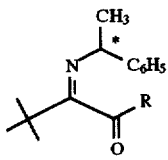   I wherein

R is OH, $NH_2$, lower-alkyl-NH or phenyl-lower-alkyl-NH, together with the enantiomers and diastereomers thereof. As a preferred embodiment, phenyl-lower alkyl-NH is preferably

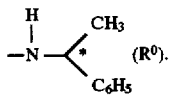

As used herein, "lower-alkyl" denotes straight-chain or branched alkyl groups with up to 6, preferably up to 4, C atoms, such as methyl, ethyl or tert-butyl. 1-Phenylethyl is an example of lower-alkyl substituted by phenyl.

Examples of compounds of formula I embodied by the present application include, for example:

for when R is OH, (S)-3,3-dimethyl-2-(1-phenylethylimino)-butyric acid and (R)-3,3-dimethyl-2-(1-phenylethylimino)-butyric acid;

for when R is $NH_2$, (S)-3,3-dimethyl-2-(1-phenylethylimino)-butyramide and (R)-3,3-dimethyl-2-(1-phenylethylimino)-butyramide;

for when R is lower-alkyl-NH and in particular when R is tert.-butyl-NH, (S)-N-tert.-butyl-3,3-dimethyl-2-(1-phenylethylimino)-butyramide and (R)-N-tert.-butyl-3,3-dimethyl-2-(1-phenylethylimino)-butyramide;

and for when R is methyl-NH, (S)-3,3,N-trimethyl-2-(1-phenylethylimino)-butyramide and (R)-3,3,N-trimethyl-2-(1-phenylethylimino)-butyramide;

and for when R is phenyl-lower-alkyl-NH and in particular when R is

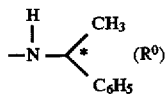

(S)-3,3-dimethyl-N-[(S)-1-phenylethyl]-2-(1-phenylethylimino)-butyramide and (R)-3,3-dimethyl-N-[(R)-1-phenylethyl]-2-(1-phenylethylimino)-butyramide.

The invention is also concerned with a process for making compounds of the formula

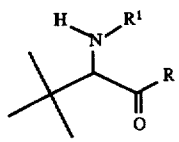   II wherein $R^1$ is H or a group of the formula

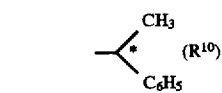

where R is as defined above.

This process comprises catalytically hydrogenating a compound of formula I, the catalyst being a noble metal catalyst, preferably being a platinum or palladium catalyst and most preferably a palladium catalyst.

The compounds of formula II are valuable intermediates in the synthesis of therapeutic pseudopeptides. Thus, the compounds II in which R is a group of formula $R^{10}$ (see formula IIa hereinafter) can be converted as described hereinafter into the compounds II in which $R^1$ is H (see formula IIb). The latter compounds are described in European Patent Applications Publ. No. 497 192 and No. 664 284 as starting materials for the manufacture of collagenase inhibitors.

Optically pure tert-leucine, i.e. the compound of formula II in which R is OH and $R^1$ is H (see compound IIb hereinafter in which R is OH) is a commercially available product which can be used in various asymmetric syntheses, e.g. in the manufacture of optically pure non-natural amino acids.

Further examples of compounds of formula II include:

(S)-tert-Leucinamide,
(S)-N-methyl-tert-leucinamide,
(R)-N-methyl-tert-leucinamide,
(S)-N-tert-butyl-tert-leucinamide,
(S)-3,3,N-trimethyl-2-[(S)-1-phenyl-ethylamino]-butyramide,
(R)-3,3,N-trimethyl-2-[(S)-1-phenyl-ethylamino]-1-butyramide and
(S)-N-[(S)-1-phenyl-ethyl]-tert-leucinamide.

The hydrogenation of compound I→compound II is carried out in a solvent, such as methanol, in the presence of a heterogeneous catalyst, which conveniently consists of a noble metal, such as Pd or Pt, on a carrier, such as charcoal, and which can be modified with a base, such as triethylamine. Conveniently, the hydrogenation is carried out at a temperature up to about 80° C. under a pressure of up to about 5 bar. The hydrogenation of a compound of formula I in which R is OH is conveniently carried out with a Pd catalyst in methanol in the presence of an acid, such as acetic acid or preferably tartaric acid. Optically pure tert-leucine is thereby obtained.

The hydrogenation proceeds via the compounds of the formula

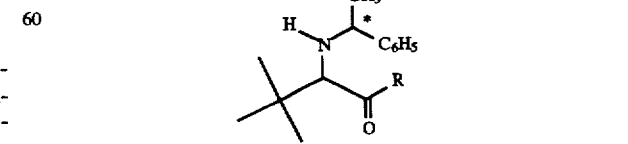   IIa which can be converted by hydrogenolysis either in situ or after isolation into the compounds of the formula

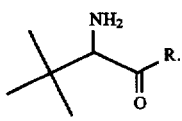

When a Pt catalyst or a Pd catalyst modified with a base is used, the compound IIa can be isolated readily and can be conveniently hydrogenolyzed to the compound IIb using a Pd catalyst.

A compound of formula II in which $R^1$ is H and R is $NH_2$, lower-alkyl-NH or phenyl-lower-alkyl-NH can be hydrolyzed to tert-leucine with an acid, such as hydrochloric acid.

The compounds of formula I can be made in accordance with the invention by a) for making a compound of formula I in which R is OH, reacting trimethylpyruvic acid

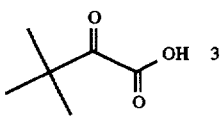

with a compound of the formula

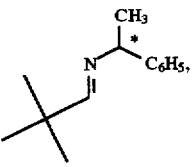

b) for making a compound of formula I in which R is $NH_2$, lower-alkyl-NH or phenyl-lower-alkyl-NH, especially for when R is $R^0$, reacting a compound of the formula

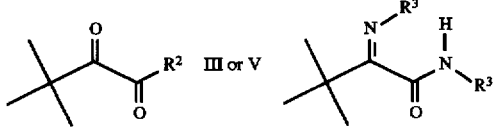

or a mixture thereof, wherein $R^2$ is $NH_2$, lower-alkyl-NH, phenyl-lower-alkyl-NH or lower-alkoxy and $R^3$ is lower-alkyl, with an amine of the formula

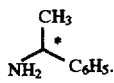

Reaction a) is carried out in a solvent, such as diethyl ether, at a temperature between 0° C. and room temperature.

Reaction b) is carried out in an apolar solvent, such as benzene, toluene or xylene, at a temperature up to the reflux temperature of the reaction mixture, with the resulting water as well as the lower-alkanol which may be formed or the lower-alkyl amine which may be formed being preferably distilled off azeotropically.

Compound III in which $R^2$ is lower-alkoxy is obtained a) by esterifying trimethylpyruvic acid of the formula

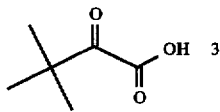

for example in the presence of a strong acid, such as hydrochloric acid, in an apolar solvent, such as toluene, using the corresponding lower-alkanol ($R^2$—H) at a temperature up to the reflux temperature of the reaction mixture, or b) by a Grignard reaction between the corresponding oxalic acid diester $(C(O)—R^2)_2$ in a solvent, such as diethyl ether, with a solution of tert-butylmagnesium chloride in the same solvent while cooling, e.g. to $-10°$ C.

By reaction of compound III, prepared as described above, with a lower-alkylamine or phenyl-lower-alkylamine in a solvent, such as ethanol, there is obtained a ketoamide III in which $R^2$ is $NH_2$, lower-alkyl-NH or phenyl-lower-alkyl, possibly in admixture with a compound V.

A ketoamide III or a mixture thereof with V can be separated into its components or preferably converted by reaction with a compound of formula VI above into the corresponding compound of formula I in which R is lower-alkylamino (NH—$R^3$). By reaction of compound III with compound VI there is obtained the corresponding compound of formula I in which R stands for $R^0$.

The following Examples a) to n) and 1 to 12 illustrate making the compounds of formula I and, respectively, their hydrogenation to the compounds of formula II.

a) 125 ml of toluene were added to 250 g of an aqueous solution of trimethylpyruvic acid (1.108 mol) and 62.5 ml (0.38 mol) of conc. hydrochloric acid. The reaction mixture was heated under reflux on a water separator for 2 hours. The distillate was extracted with toluene and the toluene phases were added to the reaction mixture. 100 ml of ethanol were added to the reaction mixture and this was heated under reflux on a water separator for 21 hours. The aqueous distillate was extracted with toluene and the toluene phases were added to the reaction mixture. Then, a saturated sodium bicarbonate solution was added and the reaction mixture was stirred for 30 minutes. After phase separation the aqueous phase was extracted with toluene. The combined organic phases were washed with a sodium chloride solution, dried over sodium sulfate and filtered. The sodium sulfate was washed with toluene. The solution obtained contains pure ethyl trimethylpyruvate.

b) 300 ml of a solution of 33% methylamine in ethanol (2.409 mol) were added to this solution. The reaction mixture was stirred for 7 hours and then concentrated. The product (168.3 g) contains 35% 3,3,N-trimethyl-2-oxo-butyramide and 64% 3,3,N-trimethyl-2-methylimino-butyramide.

c) 147.5 g (1.217 mol) of (S)-1-phenylethylamine were added to a solution of the product from b) in 125 ml of toluene. The reaction mixture was boiled under reflux on a water separator for 6 hours, then evaporated and dried. 295.3 g of (S)-3,3,N-trimethyl-2-(1-phenylethylimino)-butyramide were obtained.

For purification, a solution of the product from c) in 900 ml of toluene was filtered over basic aluminum oxide. The filtrate was evaporated, the residue was crystallized from hexane at 0° C. and washed with hexane. There were obtained 210.8 g of pure (S)-3,3,N-trimethyl-2-(1-phenylethylimino)-butyramide, m.p. 121.2°–121.4° C., $[\alpha]= -75°$ (c=1.0, $CHCl_3$).

d) When (R)-1-phenylethylamine was used in place of the (S)-1-phenylethylamine used under c) there was obtained (R)-3,3,N-trimethyl-2-(1-phenylethylimino)-butyramide, m.p. 119.5°–120° C., [α]=+75° (c=1.0, CHCl$_3$).

e) A solution of 12 g (82 mmol) of diethyl oxalate in 100 ml of diethyl ether was cooled to −18° C. A solution of 40 ml (80 mmol) of 2M tert-butylmagnesium chloride in diethyl ether was added within 2 hours in such a manner that the temperature remains below −10° C. After stirring at −10° C. for one hour the reaction mixture was hydrolyzed with 40 ml of a saturated ammonium chloride solution at 0° C. and stirred at room temperature for one hour. After working up there were obtained 220 ml of an ether solution containing ethyl trimethyl-pyruvate. This ester was 75% pure according to analysis by gas chromatography.

f) 20 ml (160 mmol) of a 33% solution of methylamine in ethanol were added to this solution at room temperature. After stirring for 18 hours the mixture was evaporated to give 9.1 g of an oil containing 69% 3,3,N-trimethyl-2-oxo-butyramide and 13% 3,3,N-trimethyl-2-methylimino-butyramide.

g) This oil was dissolved in 30 ml of toluene and treated with 12.1 g (100 mmol) of (S)-1-phenylethylamine. The reaction mixture was boiled under reflux on a water separator for 46 hours. After evaporation and crystallization from hexane there were obtained 8.84 g (45% based on tert-butyl-MgCl) of (S)-3,3,N-trimethyl-2-(1-phenylethylimino)-butyramide, m.p. 118.6°–118.8° C., [α]=−74.4 (c=0.9, CHCl$_3$).

h) A solution of 15 g (95 mmol) of ethyl trimethyl-pyruvate and 50 g (413 mmol) of (S)-1-phenylethylamine in 50 ml of xylene was boiled under reflux on a water separator for 18 hours. Subsequently, the solvent was distilled off and excess amine was removed at 120° C. in a vacuum. After crystallization of the distillation residue from 125 ml of hexane there were obtained 14.3 g (45%) of (S)-3,3-dimethyl-N-[(S)-1-phenylethyl]-2-(1-phenylethylimino)-butyramide of melting point 96°–97° C. [α]=−58.9 (c=1.0, CHCl$_3$).

i) The procedure described under h) was carried out using 15 g of ethyl trimethyl-pyruvate and 50 g of (R)-1-phenylethylamine. There were isolated 14.9 g of (47%) of (R)-3,3-dimethyl-N-[(R)-1-phenylethyl]-2-(1-phenylethylimino)-butyramide of melting point 95°–96° C. [α]=+59.6 (c=1.0, CHCl$_3$).

j) 8.9 g (47 mmol) of (S)-(2,2-dimethylpropylidene)-(1-phenylethyl)-amine (J. L. Fauchure, C. Petermann, Helv. Chim. Acta 1980, 63, 824) were dissolved in 10 ml of diethyl ether with the exclusion of moisture. 8.1 g (50 mmol) of trimethylpyruvic acid in 10 ml of diethyl ether were added dropwise to this solution while cooling with ice. Subsequently, the mixture was stirred at 0° C. for a further 2 hours and at room temperature for 6 hours. Colorless crystals form over 2 days and these were suspended in 50 ml of diethyl ether, filtered off and washed twice with 5 ml of diethyl ether each time. After drying in a vacuum there were obtained 8.9 g (81%) of (S)-3,3-dimethyl-2-(1-phenylethylimino)-butyric acid (internal salt) of melting point 135°–136° C. [α]=−14.4 (c=0.16, CH$_2$Cl$_2$).

k) (R)-3,3-Dimethyl-2-(1-phenylethylimino)-butyric acid (internal salt) can be prepared from (R)-(2,2-dimethylpropylidene)-(1-phenylethyl)-amine and trimethylpyruvic acid in an analogous manner.

l) A solution of 30.0 g (162 mmol) of N-tert-butyl-3,3-dimethyl-2-oxo-butyramide (D. Seyferth, R. C. Hui, Tetrahedron Lett. 1984, 25, 5251) and 50 g (413 mmol) of (S)-1-phenylethylamine in 150 ml of toluene was boiled under reflux on a water separator for 20 hours. Subsequently, the solvent and excess amine were removed in a vacuum. The residue was treated with 200 ml of hexane at 0° C. and stirred. After filtration of the suspension and concentration in a vacuum the residual oil was distilled. There were obtained 37.2 g (80%) of (S)-N-tert-butyl-3,3-dimethyl-2-(1-phenylethylimino)-butyramide of boiling point 140° C. at 0.3 mbar. [α]=−40.7 (c=1.0, CHCl$_3$).

m) The procedure described under l) was carried out using 7.5 g of N-tert-butyl-3,3-dimethyl-2-oxo-butyramide and 15 g of (R)-1-phenylethylamine. There were isolated 6.8 g (58%) of (R)-N-tert-butyl- 3,3-dimethyl-2-(1-phenylethylimino)-butyramide of boiling point 120° at 0.2 mbar. [α]=+40.9 (c=1.0, CHCl$_3$).

n) A solution of 35.0 g (271 mmol) of 3,3-dimethyl-2-oxobutyramide and 75.0 g (619 mmol) of (S)-1-phenylethylamine in 250 ml of toluene was boiled under reflux on a water separator for 92 hours. Subsequently, the solvent and excess amine were removed in a vacuum. The residual oil was crystallized from 300 ml of hexane. 51 g of crude material of melting point 96°–97° C. were obtained. After recrystallization from 400 ml of hexane there were obtained 42.7 g (68%) of analytically-pure (S)-3,3-dimethyl-2-(1-phenylethylimino)-butyramide of melting point 100°–101° C. [α]=−58.5 (c=1.0, CHCl$_3$).

o) The procedure described under n) was carried out using 5.0 g of 3,3-dimethyl-2-oxo-butyramide and 10.0 g of (R)-1-phenylethylamine. After a single crystallization from hexane there were isolated 6.0 g (67%) of (R)-3,3-dimethyl-2-(1-phenylethylimino)-butyramide of melting point 100°–101° C. [α]=+61.4 (c=0.8, CHCl$_3$).

EXAMPLE 1

A solution of 100.0 g (406 mmol) of (S)-3,3,N-trimethyl-2-(1-phenylethylimino)-butyramide in 775 ml of methanol was hydrogenated in a 2 l autoclave in the presence of 5 g of 5 percent Pd/C at 40° C. and at a pressure of 1 bar for 7 hours. Re-hydrogenation was carried out for 6 hours at 70° C. and under a pressure of 2 bar in order to complete the hydrogenolysis. After cooling the catalyst was filtered off and the filtrate was evaporated to dryness: 58.3 g (99.6%) of white crystals with 99.6% N-methyl-tert-leucinamide content, e.e. 97.2%. Recrystallization from 425 ml of cyclohexane yields (S)-N-methyl-tert-leucinamide as white crystals, m.p. 90°–93° C., [α]=−40.8 (c=1, CHCl$_3$), 99.3% e.e. In order to determine the e.e value, the product was derivatized with (−)-camphanoyl chloride and the diastereomer mixture was analyzed by gas chromatography.

EXAMPLE 2

A solution of 3.0 g (12.18 mmol) of (S)-3,3,N-trimethyl-2-(1-phenylethylimino)-butyramide in 50 ml of methanol was hydrogenated in a 380 ml autoclave in the presence of 0.5 g of 5 percent Pd/C at 80° C. and 2.0 bar initial pressure for 5 hours. Thereafter, the pressure was dropped to 1.5 bar. After cooling the catalyst was filtered off and the filtrate was evaporated to dryness: 1.75 g (99.6%) of white crystals containing 97.0% (S)-N-methyl-tert-leucinamide, 93.7% e.e.

EXAMPLE 3

A solution of 3.0 g (12.18 mmol) of (R)-3,3,N-trimethyl-2-(1-phenylethylimino)-butyramide in 50 ml of methanol was hydrogenated in a low pressure hydrogenation apparatus in the presence of 0.5 g of 5 percent Pd/C at 40° C. under normal pressure for 21 hours. After cooling the catalyst was filtered off and the filtrate was evaporated to dryness: 1.75 g (99.6%) of white crystals containing 99.5% (R)-N-methyl-tert-leucinamide, 98.6% e.e.

EXAMPLE 4

A solution of 24.6 g (100 mmol) of (S)-3,3,N-trimethyl-2-(1-phenylethylimino)-butyramide in 180 ml of methanol and 10 ml of triethylamine was hydrogenated in a 380 ml autoclave in the presence of 2.5 g of 5 percent Pd/C at 20° C. and a pressure of 5 bar for 47 hours. After releasing the pressure the catalyst was filtered off and the filtrate was evaporated to dryness. There were obtained 22.5 g (90.6%) of white crystals containing 85.0% (S)-3,3, N-trimethyl-2-((S)-1-phenylethylamino)-butyramide and 7.7% (R)-3,3,N-trimethyl-2-((S)-1-phenylethylamino)-butyramide. Two-fold recrystallization from 160 ml and 100 ml of diisopropyl ether yielded 11.5 g (51.3%) of (S)-3,3,N-trimethyl-2-[(S)-1-phenylethylamino]-butyramide as white crystals, m.p. 159°–160° C., $[\alpha]$=−107.9 (c=1, CHCl$_3$).

EXAMPLE 5

A solution of 12.4 g (50 mmol) of (S)-3,3,N-trimethyl-2-[(S)-1-phenylethylamino]-butyramide in 206 ml of methanol was hydrogenated in a 380 ml autoclave in the presence of 1.2 g of 5 percent Pd/C at 50° C. and under a pressure of 4 bar for 6 hours. After pressure release the catalyst was filtered off and the filtrate was evaporated to dryness. There were obtained 7.1 g (98.5%) of (S)-N-methyl-tert-leucinamide as white crystals, 99.2% e.e.

EXAMPLE 6

A solution of 24.6 g (100 mmol) of (S)-3,3,N-trimethyl-2-(1-phenylethylimino)-butyramide in 190 ml of methanol was hydrogenated in a 380 ml autoclave in the presence of 2.5 g of 5 percent Pd/C at 20° C. and a constant pressure of 5 bar for 23 hours. After pressure release the catalyst was filtered off and the filtrate was evaporated to dryness. There were obtained 23.2 g (93.3%) of white crystals containing 85.2% (R)-3,3,N-trimethyl-2-[(S)-1-phenylethylamino]-butyramide and 12.7% (S)-3,3,N-trimethyl-2-[(S)-1-phenylethylamino]-butyramide. Two-fold recrystallization from 90 ml and 85 ml of diisopropyl ether yielded 11.8 g (50.9%) of (R)-3,3,N-trimethyl-2-[(S)-1-phenylethylamino]-butyramide as white crystals, m.p. 107°–108° C., $[\alpha]$=+20.4 (c=1, CHCl$_3$).

EXAMPLE 7

A solution of 20.0 g (69.3 mmol) of (S)-N-tert-butyl-3,3-dimethyl-2-(1-phenylethylimino)-butyramide in 155 ml of methanol was hydrogenated in a low pressure hydrogenation apparatus in the presence of 12.5 g of 5 percent Pd/C at 40° C. and normal pressure for 51 hours. After cooling the catalyst was filtered off and the filtrate was evaporated to dryness: 11.9 g (92.2%) of white crystals containing 94.4% (S)-N-tert-butyl-tert-leucinamide, 92.5% e.e. Recrystallization from 50 ml of hexane yielded 7.8 g (66.0%) of (S)-N-tert-butyl-tert-leucinamide as white crystals, m.p. 78°–80° C., $[\alpha]$=−32.2 (c=1, CHCl$_3$), >98% e.e.

EXAMPLE 8

A solution of 12.0 g (51.7 mmol) of (S)-3,3-dimethyl-2-(1-phenylethylimino)-butyramide in 200 ml of methanol was hydrogenated in a low pressure hydrogenation apparatus in the presence of 2.0 g of 5 percent Pd/C at 40° C. and normal pressure for 6.5 hours. After cooling the catalyst was filtered off and the filtrate was evaporated to dryness: 6.7 g (99.5%) of white crystals containing 90.8% (S)-tert-leucinamide, 97.0% e.e. Recrystallization from 40 ml of cyclohexane yielded 5.3 g (78.5%) of (S)-tert-leucinamide as white crystals, m.p. 104°–105° C., $[\alpha]$=−23.2 (c=1, CHCl$_3$), 96.9% e.e.

EXAMPLE 9

A solution of 3.0 g (8.9 mmol) of (S)-3,3-dimethyl-N-[(S)-1-phenylethyl]-2-(1-phenylethylimino)-butyramide in 200 ml of methanol was hydrogenated in a low pressure hydrogenation apparatus in the presence of 2.0 g of 5 percent Pd/C at 40° C. and normal pressure for 6.5 hours. After cooling the catalyst was filtered off and the filtrate was evaporated to dryness: 6.7 g (99.5%) of white crystals containing 90.8% (S)-N-[(S)-1-phenylethyl]-tert-leucinamide, m.p. 57°–60° C., $[\alpha]$=−103.1 (c=1, CHCl$_3$), 97.0% e.e.

EXAMPLE 10

A solution of 2.0 g (8.6 mmol) of (S)-3,3-dimethyl-2-(1-phenylethylimino)-butyric acid (internal salt) in 60 ml of methanol was hydrogenated in a low pressure hydrogenation apparatus in the presence of 2.6 g (43 mmol) of acetic acid and 1.0 g of 5 percent Pd/C at 40° C. under normal pressure for 27 hours. After cooling the catalyst was filtered off and the filtrate was evaporated to dryness: 1.64 g of a white foam, 74.6% e.e. Digestion in 15 ml of ethanol yielded 0.85 g (74.5%) of white crystals containing 99.5% (S)-tert-leucine, 74.2% e.e.

EXAMPLE 11

A solution of 2.0 g (8.6 mmol) of (S)-3,3-dimethyl-2-(1-phenylethylimino)-butyric acid (internal salt) in 60 ml of methanol was hydrogenated in a low pressure hydrogenation apparatus in the presence of 1.3 g (8.6 mmol) of D-(−)-tartaric acid and 1.0 g of 5 percent Pd/C at 40° C. and normal pressure for 24 hours. After cooling the catalyst was filtered off and the filtrate was evaporated to dryness: 2.55 g of white foam, 84.1% e.e. Digestion in 15 ml of ethanol yielded 0.86 g (75.4%) of white crystals containing 37.9% tartaric acid and 61.7% (S)-tert-leucine, 100% e.e.

EXAMPLE 12

A solution of (S)-N-methyl-tert-leucinamide in 100 ml of a 6N solution of HCl/CH$_3$COOH (1:1) was heated under reflux for 14 days. Then, the mixture was evaporated, the residue was chromatographic over AMBERLITE. Evaporation and drying gave 750 mg (41%) of (S)-tert-leucine, $[\alpha]$=+6.2 (c=1.62, 5N HCl), 97% e.e.

EXAMPLE 13

A solution of 1.0 g of (S)-N-tert-butyl-tert-leucinamide in 10 ml of 6N HCl was heated at 80° C. for 2 days. The solution was evaporated to dryness. The residue was dissolved in water and chromatographed over AMBERLITE. There were obtained 550 mg (78%) of (S)-tert-leucine, 100% e.e.

EXAMPLE 14

In a manner analogous to Example 13, 1 g of (S)-tert-leucinamide was hydrolyzed to 250 mg of (S)-tert-leucine, $[\alpha]$=+6.5 (c=1.33, 5N HCl), 98% e.e.

We claim:
1. A compound of the formula

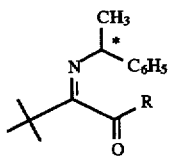

wherein
R is OH, NH$_2$, lower-alkyl-NH or phenyl-lower-alkyl-NH and the enantiomers and diastereomers thereof.

2. The compound of claim 1 wherein R is OH.
3. The compound of claim 2, (S)-3,3-dimethyl-2-(1-phenylethylimino)butyric acid.
4. The compound of claim 2, (R)-3,3-dimethyl-2-(1-phenylethylimino)-butyric acid.
5. The compound of claim 1 wherein R is NH$_2$.
6. The compound of claim 5, (S)-3,3-dimethyl-2-(1-phenylethylimino)-butyramide.
7. The compound of claim 5, (R)-3,3-dimethyl-2-(1-phenylethylimino)-butyramide.
8. The compound of claim 1 wherein R is lower-alkyl-NH.
9. The compound of claim 8 wherein R is tert.-butyl-NH.
10. The compound of claim 9, (S)-N-tert.-butyl-3,3-dimethyl-2-(1-phenylethylimino)-butyramide.
11. The compound of claim 9, (R)-N-tert.-butyl-3,3-dimethyl-2-(1-phenylethylimino)-butyramide.
12. The compound of claim 8 wherein R is methyl-NH.
13. The compound of claim 12, (S)-3,3-N-trimethyl-2-(1-phenylethylimino)-butyramide.
14. The compound of claim 12, (R)-3,3-N-trimethyl-2-(1-phenylethylimino)-butyramide.
15. The compound of claim 1 wherein R is phenyl-lower-alkyl-NH.
16. The compound of claim 15 wherein R is

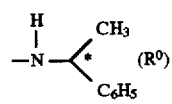

17. The compound of claim 16, (S)-3,3-dimethyl-N-[(S)-1-phenylethyl]-2-(1-phenylethylimino)-butyramide.
18. The compound of claim 16, (R)-3,3-dimethyl-N-[(S)-1-phenylethyl]-2-(1-phenylethylimino)-butyramide.

* * * * *